United States Patent
Riva et al.

(10) Patent No.: US 7,316,918 B2
(45) Date of Patent: Jan. 8, 2008

(54) PROCESS FOR THE PREPARATION OF (−) MODAFINIL

(75) Inventors: Sergio Riva, Seveso (IT); Paola Fassi, Vittuone (IT); Pietro Allegrini, San Donato Milanese (IT); Gabriele Razzetti, Sesto S. Giovanni (IT)

(73) Assignee: Dipharma S.p.A., Mereto di Tomba (IT)

( * ) Notice: Subject to any disclaimer, the term of this patent is extended or adjusted under 35 U.S.C. 154(b) by 0 days.

(21) Appl. No.: 11/581,580

(22) Filed: Oct. 17, 2006

(65) Prior Publication Data

US 2007/0087422 A1    Apr. 19, 2007

(30) Foreign Application Priority Data

Oct. 18, 2005  (IT) ................. MI2005A1971

(51) Int. Cl.
*C12P 13/02*  (2006.01)
*C12P 11/00*  (2006.01)

(52) U.S. Cl. ........................ 435/129; 435/130

(58) Field of Classification Search ............... 435/129, 435/130

See application file for complete search history.

(56) References Cited

U.S. PATENT DOCUMENTS

| | | | | |
|---|---|---|---|---|
| 4,177,290 A * | 12/1979 | Lafon | ........................ | 514/618 |
| 4,927,855 A * | 5/1990 | Lafon | ........................ | 514/618 |
| 5,801,006 A * | 9/1998 | Kaufman | ..................... | 435/15 |
| 7,125,693 B2 * | 10/2006 | Davis et al. | ................ | 435/128 |
| 7,163,815 B2 * | 1/2007 | Riebel-Bommarius et al. | .. | 435/190 |
| 2004/0067565 A1 * | 4/2004 | Schmid et al. | .............. | 435/147 |
| 2007/0026507 A1 * | 2/2007 | Olivo et al. | ................ | 435/129 |

OTHER PUBLICATIONS

Malito et al "Proc. Natl. Acad.Sci.USA" 101 pp. 13157-13162.*

* cited by examiner

*Primary Examiner*—Herbert J. Lilling
(74) *Attorney, Agent, or Firm*—Young & Thompson

(57) ABSTRACT

An enzymatic process for the preparation of intermediates useful in the synthesis of (−) modafinil.

18 Claims, No Drawings

PROCESS FOR THE PREPARATION OF (−) MODAFINIL

FIELD OF THE INVENTION

The present invention relates to a novel enzymatic process for the preparation of (−) modafinil and intermediates useful for its synthesis.

TECHNOLOGICAL BACKGROUND (−) Modafinil, (−) benzhydrylsulfinylacetamide, is a psychotropic agent, used in the treatment of idiopathic narcolepsy.

According to U.S. Pat. No. 4,927,855, its preparation comprises:
a) oxidation of benzhydrylthioacetic acid to give (±) benzhydrylsulfinylacetic acid; b) reaction of this with (−) α-methylbenzylamine to give (−) α-methylbenzylamine (−) benzhydrylsulfinylacetate; c) conversion of this to (−) benzhydrylsulfinylacetic acid; and finally d) amidation to obtain (−) benzhydrylsulfinylacetamide. A key intermediate in this preparation is (−) benzhydrylsulfinylacetic acid. According to the above described process, the yield in the key intermediate is approx. 40%, with an approx. 99% enantiomeric excess.

There is therefore a need for an alternative synthesis of (−) benzhydrylsulfinylacetic acid, which can be used industrially and provides higher yields.

SUMMARY OF THE INVENTION

Object of the present invention is an enzymatic process for the preparation of (−) benzhydrylsulfinylacetic acid, and its use in the preparation of (−)-benzhydrylsulfinylacetamide.

According to invention, the following definitions apply:
1.0 unit of PHENYLACETONE MONOOXYGENASE is the amount of enzyme which catalyzes the conversion of 1.0 μmol of thioanisole to thioanisole sulfoxide in 1 minute at pH 8.5 and at room temperature.
1.0 unit of GLUCOSE 6 PHOSPHATE DEHYDROGENASE is the amount of enzyme which oxidizes 1.0 μmol of glucose-6-phosphate to 6-phosphogluconate in 1 minute with NADP as a cofactor at pH 7.4 and at a temperature of 25° C.

DETAILED DISCLOSURE OF THE INVENTION

Object of the present invention is a process for the preparation of (−) benzhydrylsulfinylacetic acid, which comprises contacting benzhydrylthioacetic acid and phenylacetone monooxygenase.

The reaction is carried out in the presence of such cofactors as NADP (Nicotinamide Adenine Dinucleotide phosphate) or NADPH, and of a system for regenerating the cofactor in the reduced form.

Regeneration systems which can be used are, for example, glucose-6-phosphate and glucose-6-phosphate dehydrogenase; isopropanol and alcohol dehydrogenase from *Thermoanaerobium brockii*; glucose and glucose dehydrogenase; or malic acid and malate dehydrogenase; preferably glucose-6-phosphate and glucose-6-phosphate dehydrogenase.

The enzyme phenylacetone monooxygenase is, for example, the enzyme "PAMO", known from Malito E. et al in Proc. Natl. Acad. Sci. USA 101, 13157-13162, which discloses its preparation via recombinant DNA.

The concentration of substrate in the solution approximately ranges from 0.1 M to 0.001 M, preferably from about 0.015 M to about 0.005 M, and is more preferably about 0.008 M.

The ratio of phenylacetone monooxygenase to substrate approximately ranges from 1 U/mg of substrate to 0.01 U/mg of substrate, and preferably ranges from about 0.8 U/mg of substrate to about 0.05 U/mg of substrate, more preferably about 0.4 U/mg of substrate.

The ratio of cofactor, for example NADP or NADPH, to substrate stoichiometric approximately ranges from 1 to 0.01 mols/mole of substrate, and preferably ranges from about 0.1 to about 0.02 mols/mole of substrate, more preferably about 0.03 mols/mole of substrate.

The concentration of glucose-6-phosphate in the solution approximately ranges from 0.1 M to 0.001 M, preferably from about 0.02 M to about 0.005 M, and is more preferably about 0.011 M.

The ratio of glucose-6-phosphate dehydrogenase to phenylacetone monooxygenase units approximately ranges from 1 U to 25 U/U of phenylacetone monooxygenase, preferably from about 5 U to 15 U/U of phenylacetone monooxygenase, and is more preferably 10 U/U of phenylacetone monooxygenase.

The reaction is typically carried out in aqueous buffered solution at pH approx. ranging from 8.0 to 10.0, preferably approx. from 8.5 to 9.5.

Examples of buffered solutions useful for this purpose are TRIS [tris(hydroxymethyl)aminomethane]/HCl, phosphate buffer, ammonium carbonate, ethanolamine/HCl, sodium tetraborate $(Na_2B_4O_7)$/HCl.

If desired, the reaction can be carried out in the presence of a co-solvent, selected from, for example, alkanols, for instance a $C_1$-$C_4$ alkanol, preferably methyl alcohol or isopropanol; ethers, such as dioxane; or ketones, such as acetone. The ratio of co-solvent to buffered solution volume approximately ranges from 30 to 5, preferably from 15 to 8.

The reaction can be carried out at a temperature approx. ranging from 15 to 80° C., preferably from about 20 to about 70° C., typically at about 25° C.

(−) Benzhydrylsulfinylacetic acid is obtained in 100% yield, in an enantiomeric excess equal to or higher than 50%, in particular approx. 91% (95.5:4.5 ratio).

If desired, the resulting (−) benzhydrylsulfinylacetic acid can be purified by resolution with (−) α-methylbenzylamine, as it is well-known in the art, to provide the compound in an enantiomeric excess equal to or higher than 99%, suitable for the industrial use. The overall yield, calculated on the starting benzhydrylthioacetic acid, is higher than 65%, typically equal to or higher than 85%.

A further object of the invention is a process for the preparation of (−) benzhydrylsulfonylacetamide which comprises:
a) contacting benzhydrylthioacetic acid and phenylacetone monooxygenase, under conditions effective to obtain (−) benzhydrylsulfinylacetic acid, which is optionally subsequently purified; and
b) converting (−) benzhydrylsulfinylacetic acid into (−)-benzhydrylsulfonylacetamide.

According to the invention, step a) is effected as reported above; and step b) can be carried out, for example, as disclosed in WO 03/095423.

The following examples illustrate the invention.

EXAMPLE 1

(−) Benzhydrylsulfinylacetic Acid 1 mg of benzhydrylthioacetic acid and "PAMO" (0.4 unit, 20 μl) are placed in 0.5 ml of TRIS/HCl buffer solution (50 mM) at pH=9. NADP (0.1 mg), glucose-6-phosphate (1.8 mg) and glucose-6-phosphate dehydrogenase (10 μl) are added thereto. After about 24 hours the reaction is completed and (−) benzhydrylsulfinylacetic acid is obtained in an approx. 100% yield and a 77% enantiomeric excess (enantiomeric ratio: 88.5:11.5).

EXAMPLE 2

(−) Benzhydrylsulfinylacetic Acid

The procedure reported in Example 1 is repeated, using methyl alcohol (10%, 150 μl) as a co-solvent. After about 24 hours, (−) benzhydrylsulfinylacetic acid is obtained in an approx. 100% yield and an 85% enantiomeric excess (enantiomeric ratio: 92.5:7.5).

EXAMPLE 3

(−) Benzhydrylsulfinylacetic Acid 3 mg of benzhydrylthioacetic acid and "PAMO" (1.2 unit, 60 μl) are placed in 1.35 ml of TRIS/HCl buffer solution (50 mM) at pH=9 and methyl alcohol (10%, 150 μl) as a co-solvent. NADP (0.3 mg), glucose-6-phosphate (5.4 mg) and glucose-6-phosphate dehydrogenase (30 μ) are added thereto. After about 24 hours the reaction is completed and (−) benzhydrylsulfinylacetic acid is obtained in an approx. 100% yield and a 91% enantiomeric excess (enantiomeric ratio: 95.5:4.5).

Following a similar procedure, using 1 mg of benzhydrylthioacetic acid as a substrate and isopropanol as a co-solvent, (−) benzhydrylsulfinylacetic acid is obtained in a 93% enantiomeric excess.

The invention claimed is:

1. A process for the preparation of (−) benzhydrylsulfinylacetic acid, comprising reacting benzhydrylthioacetic acid and phenylacetone monooxygenase.

2. The process according to claim 1, wherein the reaction is carried out in the presence of a cofactor and of a system for regenerating the cofactor in the reduced form.

3. The process according to claim 2, wherein the cofactor is selected from NADP and NADPH.

4. The process according to claim 2, wherein the system for regenerating the cofactor in the reduced form is selected from glucose-6-phosphate and glucose-6-phosphate dehydrogenase; isopropanol and alcohol dehydrogenase from *Thermoanaerobium brockii*; glucose and glucose dehydrogenase; malic acid and malate dehydrogenase.

5. The process according to claim 2, wherein the cofactor is NADP and the system for regenerating the cofactor in the reduced form is glucose-6-phosphate and glucose-6-phosphate dehydrogenase.

6. The process according to claim 1, wherein the enzyme phenylacetone monooxygenase is a recombinant enzyme.

7. The process according to claim 1, wherein the ratio of phenylacetone monooxygenase to benzhydrylthioacetic acid approximately ranges from 1 U/mg of substrate to 0.01 U/mg of substrate.

8. The process according to claim 2, wherein the stoichiometric ratio of cofactor to benzhydrylthioacetic acid approximately ranges from 1 to 0.01 mols/mole of substrate.

9. The process according to claim 4, wherein the unit ratio of glucose-6-phosphate dehydrogenase to phenylacetone monooxygenase approximately ranges from 1 U to 25 U/U of phenylacetone monooxygenase.

10. The process according to claim 4, wherein the concentration of glucose-6-phosphate in the solution approximately ranges from 0.1 M to 0.001 M.

11. A process according to claim 1, wherein the substrate concentration in the solution approximately ranges from 0.1 M to 0.001 M.

12. A process according to claim 1, wherein the reaction is carried out in an aqueous buffered solution at pH approx. ranging from 8.0 to 10.0 and, optionally, in the presence of a co-solvent.

13. The process according to claim 12, wherein the co-solvent is selected from alkanols, ethers and ketones.

14. A process for the preparation of (−) benzhydrylsulfonylacetamide comprising:
   a) contacting benzhydrylthioacetic acid and phenylacetone monooxygenase, under suitable conditions for obtaining (−) benzhydrylsulfinylacetic acid, the optional subsequent purification thereof; and
   b) converting (−) benzhydrylsulfinylacetic acid into (−) benzhydrylsulfonylacetamide.

15. The process according to claim 3, wherein the stoichiometric ratio of cofactor to benzhydrylthioacetic acid approximately ranges from 1 to 0.01 mols/mole of substrate.

16. The process according to claim 4, wherein the stoichiometric ratio of cofactor to benzhydrylthioacetic acid approximately ranges from 1 to 0.01 mols/mole of substrate.

17. The process according to claim 5, wherein the unit ratio of glucose-6-phosphate dehydrogenase to phenylacetone monooxygenase approximately ranges from 1 U to 25 U/U of phenylacetone monooxygenase.

18. The process according to claim 5, wherein the concentration of glucose-6-phosphate in the solution approximately ranges from 0.1 M to 0.001 M.

* * * * *